United States Patent
Naik et al.

(10) Patent No.: US 12,275,695 B2
(45) Date of Patent: Apr. 15, 2025

(54) FLUID CATALYTIC CRACKING OF P-CRESOL DIMER INTO PHENOLIC MONOMERS AND PROCESS THEREOF

(71) Applicant: COUNCIL OF SCIENTIFIC AND INDUSTRIAL RESEARCH, New Delhi (IN)

(72) Inventors: Desavath V. Naik, Dehradun (IN); Samir Kumar Maity, Dehradun (IN); Bharat Singh Rana, Dehradun (IN); Pankaj Kumar Kanaujia, Dehradun (IN); Ashish Rana, Dehradun (IN); Deependra Tripathi, Dehradun (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 338 days.

(21) Appl. No.: 18/076,902

(22) Filed: Dec. 7, 2022

(65) Prior Publication Data

US 2023/0202953 A1     Jun. 29, 2023

(30) Foreign Application Priority Data

Dec. 25, 2021  (IN) .............................. 202111061090

(51) Int. Cl.
   *C07C 37/52* (2006.01)
(52) U.S. Cl.
   CPC .................................. *C07C 37/52* (2013.01)
(58) Field of Classification Search
   CPC ..................................................... C07C 37/52
   See application file for complete search history.

(56) References Cited

U.S. PATENT DOCUMENTS

| | | |
|---|---|---|
| 2,437,648 A | 3/1948 | Milas et al. |
| 2,727,926 A | 12/1955 | Kaeding et al. |
| 4,465,872 A | 8/1984 | Suzuki et al. |
| 4,532,209 A | 7/1985 | Hagedorn |
| 6,069,012 A | 5/2000 | Kayser |

FOREIGN PATENT DOCUMENTS

| | | |
|---|---|---|
| CN | 1201776 A | 12/1998 |

*Primary Examiner* — Sikarl A Witherspoon
(74) *Attorney, Agent, or Firm* — Dinsmore & Shohl LLP

(57) ABSTRACT

A fluid catalytic cracking process for p-cresol dimer to produce valuable phenolic monomers, i.e., 2-methyl phenol, 4-methyl phenol, 2,3-xylenol, and phenol, uses an equilibrium catalyst (E-cat) generated in the petroleum fluid catalytic cracking (FCC) unit. The p-cresol dimer can be processed under relatively mild conditions, while maximizing desired and minimizing undesired products. The process may include charging an equilibrium fluid catalytic cracking catalyst; heating to a predetermined cracking temperature and pressure; (c) charging a p-cresol dimer feed; (d) contacting the p-cresol dimer with the equilibrium fluid catalytic cracking catalyst; (e) condensing resulting phenolic monomer vapors to obtain phenolic monomer liquid and fluidization gas; (f) separating the phenolic monomer liquid from the fluidization gas; (g) collecting the separated phenolic monomer liquid; (h) separating the collected phenolic monomer liquid individual phenolic monomers; and (i) recycling any unconverted p-cresol dimer into the fluidized bed reactor.

9 Claims, 2 Drawing Sheets

FLUID CATALYTIC CRACKING OF P-CRESOL DIMER INTO PHENOLIC MONOMERS AND PROCESS THEREOF

CROSS-REFERENCES TO RELATED APPLICATIONS

This application claims benefit of priority under 35 U.S.C. § 119 to Indian Application No. 202111061090, filed Dec. 25, 2021, which is hereby incorporated by reference herein in its entirety.

TECHNICAL FIELD

The present application relates to fluid catalytic cracking process for the conversion of p-cresol dimer into valuable phenol monomers, i.e., 2-methyl phenol, 4-methyl phenol, 2,3-xylenol, and phenol, using equilibrium fluid catalytic cracking catalyst.

More specifically, the present application relates to conversion of p-cresol dimer into its phenolic monomers through the fluid catalytic cracking approach. The present application also discloses the disposal problems of p-cresol dimer obtained from the p-cresol process belonging to the aromatics industry (chemical sector).

BACKGROUND

The present disclosure relates to fluid catalytic cracking of p-cresol dimer to p-cresol and other more valuable phenolic products. The p-cresol dimer is a complex material consisting of various components, including 2,2'-methylenebis (4-methylphenol); 1-methyl-2-(4-methylphenoxy) benzene; 2-phenoxybenzoic acid; 4-(phenylmethyl)-phenol; and a small amount of sodium sulfate salts.

Cresol is an organic compound obtained from coal tar or petroleum, also known as methyl phenol. Increasing demand for cresol derivatives to use as a raw material or reactant in developing personal care antioxidants and chemical intermediates and expected to drive cresol demand in the forecast period. Increasing demand in the chemical industry for efficient stabilizers and the production of pesticides is also expected to drive the cresol demand.

p-Cresol is a specialty chemical and held the largest share in the cresol market in 2018. It acts as an essential raw material for plastic and an intermediate for medicines, agricultural chemicals, industrial chemicals, etc. Conventionally, the p-cresol is produced through sulfonation of toluene and chlorination of toluene. Key players operating in the global para cresol market are Tokyo Chemical Industry Co., Ltd, Atul Ltd, Sasol Phenolics, and Lanxess.

p-Cresol, a derivative of phenol, is primarily consumed in the formation of antioxidants such as butylatedhydroxytoluene (BHT), anisaldehyde, which is used in food, cosmetics, and pharmaceuticals industries. In addition, it is also used in the production of various other chemicals and their applications in different fields such as odor agents, paints & coatings, aroma ingredients, sunscreen, resins, and cleaning & degreasing agents. p-Cresol also finds many other applications in the production of plant protection agents, animal feed additives, pharmaceuticals, binding agents, adhesives, fillers, preservatives, and dyestuffs.

Reference may be made to U.S. Pat. No. 4,532,209, wherein a process for producing p-cresol in a quantitative yield described. The process involves acidifying an aqueous solution of 4-methylcyclohexane-3,5-diene-1,2-diol-1-carboxylic acid.

Reference may be made to U.S. Pat. No. 2,727,926, wherein a process for conversion of toluic acid to p-cresol in the presence of a soluble copper catalyst such as copper benzoate disclosed.

Reference may be made to U.S. Pat. No. 4,465,872, wherein a process for the production p-cresol by direct oxidation of p-tolualdehyde with peroxide in formic acid as a solvent described.

Reference may be made to U.S. Pat. No. 2,437,648, wherein a process for the production of p-cresol disclosed. The process involves oxidation of toluene with hydrogen peroxide in the presence of a catalytically active metal oxide (such as osmium tetraoxide).

Reference may be made to CN1 201776A, wherein a p-cresol manufacturing process by direct alkali fusion method from toluene-p-sulfonic acid described. p-Cresol process consists of the unit operations of toluene sulphonation, caustic fusion, and acidification. The p-cresol process has a p-cresol dimer as a by-product.

There is limited use of p-cresol dimer as a fuel, which ultimately creates ecological problems in the combustion of highly condensed aromatic compounds. Traditionally, the aromatic industries produce a considerable amount of p-cresol dimer, which is hazardous and non-flammable. Even during production of p-cresol by sulfonation or chlorination of toluene, a substantial amount of cresol dimer is produced as by-product. It is hazardous and hence the chemical industries have challenges of its disposal. Therefore, converting the dimer into its monomers and reducing p-cresol dimer by combustion would be a significant gain to these aromatic industries.

However, there is no method available in the literature to convert p-cresol dimer into monomers through either the thermal or catalytic approach. Therefore, it is a need of the hour to develop a process for converting p-cresol dimer into valuable phenol monomers. These p-cresol dimers mainly consist of about two aromatic compounds connected either by carbon-carbon or carbon-oxygen bonds. These bonds are crackable over zeolites, including the Lewis acid sites and Bronsted acid sites on the catalyst. Catalytic cracking conditions can comprise the combined heating of a p-cresol dimer to a temperature between 325 to 375° C., wherein C—C bond scission is encouraged in the presence of a catalyst.

There is a continuing research effort to develop new and improved methods for producing significant volume specialty chemicals. It is an object of this disclosure to provide a process for the production of p-cresol and other derivatives of cresol via fluidized catalytic cracking of p-cresol dimer as feedstock.

Embodiments herein provide a process for conversion of p-cresol dimer into phenolic monomers and create value addition to the product profile of the p-cresol process industry.

Embodiments herein provide an equilibrium FCC catalyst which is the most common catalyst in petroleum refinery that can be directly used for catalytic cracking reaction, and hence no need for further catalyst development.

Embodiments herein avoid the conventional method of p-cresols dimer incineration and hence to avoid environmental pollution.

Embodiments herein provide that the unconverted p-cresol dimer can be recycled to improve the more conversion in the present invention.

SUMMARY

The present disclosure provides a process for conversion of p-cresol dimer to phenolic monomers through a fluid catalytic cracking approach.

In an embodiment, the apparatus used herein is a fluidized bed reactor unit. The process comprising the steps of:
(i) Heating the p-cresol dimer at a temperature in the range between 60° C. to 100° C.,
(ii) Heating the fluidization gas at a temperature in the range between 350° C. to 400° C.,
(iii) Contacting the p-cresol dimer with an equilibrium fluid catalytic cracking catalyst at a temperature between 325° C. to 375° C.,
(iv) Condensing the catalytically cracked vapors as obtained in step (iii) in a condenser in the temperature range between 0° C. to 100° C.,
(v) Separating the condensed liquid and fluidization gases using a gas-liquid separator,
(vi) Collecting the phenolic monomers liquid as obtained in step (v) in a receiver, and
(vii) Separating phenolic monomers liquid mixture as obtained in a step (vi) into valuable individual monomers such as 2-methyl phenol, 4-methyl phenol, and 2 3-xylenol by distillation between about 180° C. to about 220° C.

In another embodiment the p-cresol dimer comprises: 2,2'-methylenebis (4-methylphenol) ranges from 40 to 46% by weight; 1-methyl-2-(4-methylphenoxy)benzene in a range from 30 to 36% by weight; 2-phenoxybenzoic acid in a range of from 8 to 12% by weight; and 4-(phenylmethyl)-phenol in a range from 2 to 4% by weight.

In another embodiment, the bottom of the fluidized bed reactor is pre-heated at a temperature in the range of 300-450° C.

In another embodiment, the reaction pressure is in the range of 0.1 to 3.0 atmospheres absolute.

In another embodiment, cracking the p-cresol dimer in the presence of equilibrium fluid catalytic cracking catalyst, obtained from a petroleum refinery fluid catalytic cracking process.

In another embodiment, the amount of equilibrium fluid catalytic cracking catalyst respective to the p-cresol dimer feed, measured as the catalyst-to-oil ratio of 0.1 to 1.0.

In another embodiment, the p-cresol dimer has a residence time in the bottom of the fluidized bed reactor of from 1.0-120.0 seconds.

In another embodiment, the phenol monomers were collected after condensation in the temperature range between 0° C. to 100° C.

In another embodiment, the obtained phenol monomers mixture is separated through distillation in the temperature range between 180° C. to 220° C.

DETAILED DESCRIPTION

Figure 1:
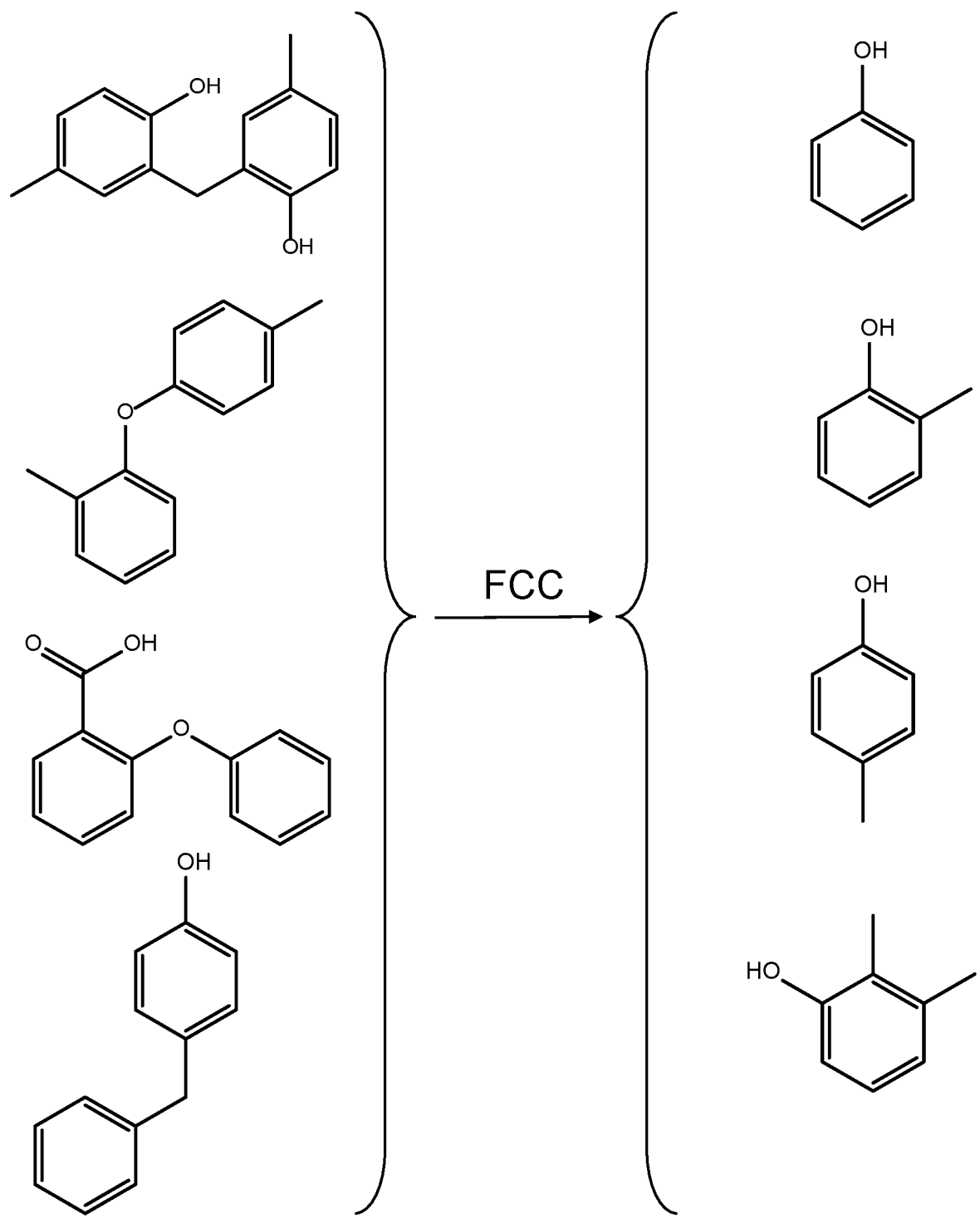
FIG. 1 illustrates the reaction scheme for the catalytic cracking of p-cresol dimer.

While particular embodiments have been illustrated and described herein, it will be understood by those skilled in the art that various changes may be made and equivalents may be substituted without departing from the scope of the claimed subject matter. In addition, many modifications may be made to adapt to a particular situation or material to the teachings of the present disclosure without departing from its scope. It is therefore intended that the appended claims cover all such changes and modifications that are within the scope of the claimed subject matter.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein. In line with the above objectives, the present disclosure relates to processes for conversion of p-cresol dimer to phenolic monomers through a fluid catalytic cracking approach.

Figure 2:
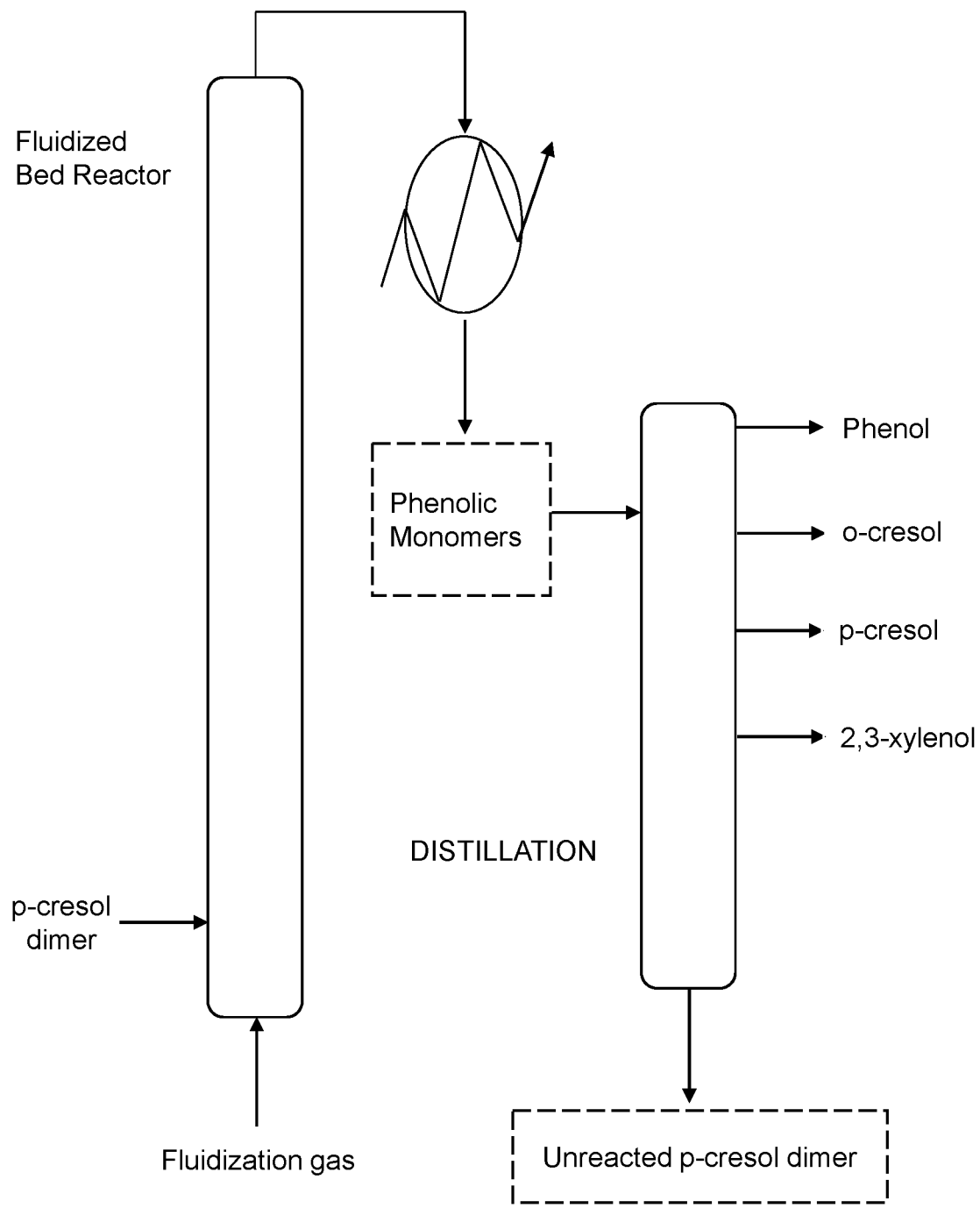
FIG. 2 illustrates the process scheme for the conversion of p-cresol dimer.

The reaction scheme is shown in FIG. 1. FIG. 2 is a schematic representation of a fluidized bed reactor unit used for the present innovation. The fluidized bed reactor unit comprises a reactor shell having a top head and bottom head with a distributor plate.

The distributor plate may be about 5μ to about 20μ size fixed in the bottom flange of the reactor. The size of the distributor plate ensures the equilibrium fluid catalytic cracking catalyst remains in the reactor and does not pass through.

A feed injector is shown extending in the radial direction into the interior of the bottom reactor, the middle of the catalyst bed. The feed injector is a removable fitting for cleaning connected to the reactor bottom.

The fluidization gas line provides inert gas, i.e., nitrogen, from the bottom end of the reactor. The inert gas is heated in the temperature range of 350-500° C., preferably 350-450° C., and most preferably 350-400° C.

The reactor top head is connected to the filter to avoid the passage of fine catalyst particles in the product stream.

Suitable processing conditions include a temperature range of 325-500° C., preferably 325-450° C., and most preferably 325-375° C., a pressure in the range of 1.0-3.0 bar, preferably 1.0-2.5 bar, and most preferably 1.0-2.0 bar.

These vapors get condensed in a series of condensers. The first condenser maintained in the temperature range of 60 to 150° C., preferably 60 to 120° C., and most preferably 60 to 100° C. The second condenser maintained in the temperature range of 0 to 20° C., preferably 0 to 10° C., and most preferably 0 to 5° C., and collected in receiving vessels. The accumulated liquid in a receiving container comprises monomers mixture, which is further fractionated according to their boiling points using a standard distillation apparatus.

The distillation apparatus may be standard ASTM-D86 with varying operating conditions, mainly cut temperatures required to separate monomers. The separated individual monomers are 2-methyl phenol, 4-methyl phenol, phenol, and 2,3-xylenol analyzed using a gas chromatograph coupled with mass spectrometric detector (GC-MS).

The p-cresol dimer is herein defined as a mixture of linear dimers 1 to 4.

"p-Cresol linear dimer 1" refers to a 2,2'-dihydroxy-5,5'-dimethylbiphenyl (or)

2,2'-methylenebis (4-methylphenol) component having structure (I).

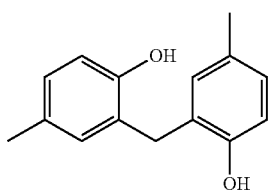

(I)

"p-Cresol linear dimer 2" refers to a 1-methyl-2-(4-methylphenoxy) benzene component having structure (II).

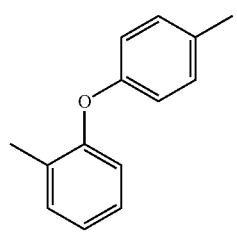

(II)

"p-Cresol linear dimer 3" refers to a 2-phenoxybenzoic acid component having structure (III).

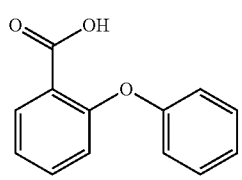

(III)

"p-Cresol linear dimer 4" refers to a 4-(phenylmethyl)-phenolcomponent having structure (IV).

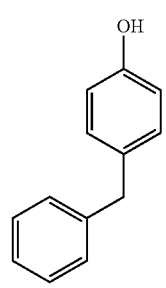

(IV)

"Fluidization gas" is herein defined as an inert gas (exemplified by nitrogen), which is not reactive under the conditions used to convert the p-cresol dimer to a valuable mixture of phenolic monomers.

"Phenolic monomer 1" refers to a phenol component having structure (V).

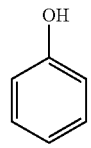

(V)

"Phenolic monomers 2" refers to a 2-methyl phenol component having structure (VI).

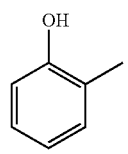

(VI)

"Phenolic monomers 3" refers to a 4-methyl phenol component having structure (VII).

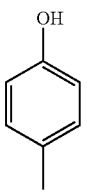

(VII)

Phenolic monomers 4" refers to a 2,3-xylenol component having structure (VIII).

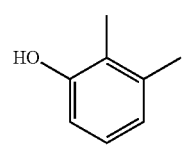

(VIII)

The value inherent in chemical compounds cracked from a p-cresol dimer, such as 2-methyl phenol, 4-methyl phenol, phenol, and 2,3-xylenol at a given state of purity.

The yield of the valuable monomers from catalytic cracking p-cresol dimer in the presence of equilibrium fluid catalytic cracking catalyst using the present method may, at times, be increased by further optimizing the process parameters and catalysts developments.

"p-Cresol dimer cracking" as used herein refers to the combined action of heat and catalyst for the p-cresol dimer cracking, which results in carbon-carbon or carbon-oxygen bond cleavage of p-cresol dimer components into its phenolic monomers such as 2-methyl phenol, 4-methyl phenol, phenol, and 2,3-xylenol.

The present disclosure provides a method for converting p-cresol dimer to its monomers wherein the p-cresol dimers comprise:

"p-cresol linear dimer 1," i.e., 2,2'-methylenebis (4-methylphenol) is 44% by weight;

"p-cresol linear dimer 2," i.e., 1-methyl-2-(4-methylphenoxy)benzene is 34% by weight;

"p-cresol linear dimer 3," i.e., 2-phenoxybenzoic acid is 10% by weight;

"p-cresol linear dimer 4," i.e., 4-(phenylmethyl)-phenol is 3% by weight.

The p-cresol dimer is a starting feedstock and partially crystalline solid. The feedstock is readily converted to a fluid upon heating in the temperature range of 20-100° C., preferably 40-100° C., and most preferably 60-100° C.

The feedstock may be added to a cracking vessel as a fluid by mechanical means of a fluid pump, preferably a positive displacement pump.

The reaction vessel may be a semi-batch type, heated fluidized bed reactor equipped with a feed heater, fluidization gas heater, condensers, and receiving vessels.

TABLE 1

Composition analysis of p-cresol dimer

| p-Cresol dimer | Composition, wt. % |
|---|---|
| 2,2'-methylenebis (4-methylphenol) | 44 |
| 1-methyl-2-(4-methylphenoxy)benzene | 34 |
| 2-phenoxybenzoic acid | 10 |
| 4-(phenylmethyl)-phenol | 3 |

TABLE 2

Physico-chemical properties of equilibrium FCC catalyst

| Properties | Equilibrium FCC catalyst |
|---|---|
| $SiO_2$ (wt. %) | 39.05 |
| $Al_2O_3$ (wt. %) | 20.8 |
| $Na_2O$ (wt. %) | 0.31 |
| Ni (ppm) | 762 |
| V (ppm) | 57 |
| Fe (ppm) | 4182 |
| Cu (ppm) | 459 |
| Surface area ($m^2/g$) | 171 |

TABLE 3

Phenolic monomers yields on cracking of p-cresol dimer at various temperatures and C/O ratio of 1.0

| | Phenolic Monomers Yield, wt. % | | |
|---|---|---|---|
| Products | @325° C. | @350° C. | @375° C. |
| phenol | 3.14 | 3.24 | 3.25 |
| o-cresol | 0.44 | 0.99 | 1.32 |
| p-cresol | 29.17 | 26.64 | 26.21 |
| 2,3-xylenol | 26.21 | 26.01 | 26.12 |
| Total | 58.97 | 56.88 | 56.92 |

TABLE 4

TABLE 4: Phenolic monomers yields after second pass cracking of p-cresol dimer at 325° C. and C/O ratios of 1.0

| | Phenolic Monomers Yield, wt. % | |
|---|---|---|
| Products | First Pass | Second Pass |
| Phenol | 3.14 | 4.11 |
| o-cresol | 0.44 | 0.57 |
| p-cresol | 29.17 | 38.22 |
| 2,3-xylenol | 26.21 | 34.35 |
| Total | 58.97 | 77.25 |

EXAMPLES

The following examples, which include preferred embodiments, will serve to illustrate the practice of this disclosure, its being understood that the particulars shown are by way of example and for purpose of illustrative discussion of preferred embodiments of the disclosure.

Example 1 p-Cresol dimer having the components of 2,2'-methylenebis (4-methylphenol); 1-methyl-2-(4-methylphenoxy) benzene; 2-phenoxybenzoic acid; and 4-(phenylmethyl)-phenol was used as a feedstock. The typical composition of the p-cresol dimer is shown in Table 1. A suitable amount of p-cresol dimer was taken into the feed vessel, and the amount of feed chosen is 420 grams, preferably 280 grams and most preferably 140 grams.

The chosen cracking reaction temperature is 375° C., preferably 350° C., and the most preferred temperature is 325° C. The chosen catalyst to oil ratio is 2.0, preferably 1.5, and the most preferred ratio is 1.0. The chosen reaction pressure is 1.5 bar, preferably 1.2 bar, and most preferably 1.1 bar. The chosen fluidization gas flow rate is 600 LPH, preferably 400 LPH, and the most preferred flow rate is 200 LPH.

The appropriate preheated equilibrium fluid catalytic cracking catalyst amount of 420 grams, preferably 280 grams, and most preferably 140 grams was loaded into the fluidized bed reactor after reaching the desired reaction temperature of 375° C., preferably 350° C., and the most preferred temperature is 325° C. Then the reactor was kept under nitrogen fluidization at a constant reaction temperature for 120 minutes to get the uniform heating of catalyst particles. A pure feedstock was contacted over a catalyst bed of thermally heated equilibrium fluid catalytic cracking particles by the mechanical means of a pump. The physico-chemical properties of the equilibrium fluid catalytic cracking catalyst are shown in Table 2.

Upon catalytic cracking, the obtained effluent stream of the reactor containing phenolic monomers vapours, which were condensed in a series of condensers. The first condenser maintained in the temperature range of 60 to 150° C., preferably 60 to 120° C., and most preferably 60 to 100° C. The second condenser maintained in the temperature range of 0 to 20° C., preferably 0 to 10° C., and most preferably 0 to 5° C. The condensed liquid product mixture was further separated into phenolic monomers such as 2-methyl phenol, 4-methyl phenol, phenol, and 2,3-xylenol by the distillation apparatus with varying cut temperatures.

The typical yields of individual phenolic monomers after desired products separation is shown in Table 3. The individual phenolic monomers are separated using the standard test method, i.e., ASTM D86, which is typically used to distillate petroleum products and liquid fuels at atmospheric pressure. During the separation, the boiling range cut for phenol, o-cresol, p-cresol, 2,3-xylenol was maintained typically at IBP-185° C., 185-195° C., 195-205° C., 205-220° C., respectively. The unreacted feed was separated in between 220-300° C. After catalytic cracking reaction, the individual phenolic monomers were identified through the GC-MS.

The fluidized bed reactor was operated in a cyclic operation mode in similar lines of U.S. Pat. No. 6,069,012. The "cyclic operation" as used herein refers to cracking followed by stripping and regeneration steps. The "stripping" as used herein refers to the process of desorption of volatiles adsorbed over the catalyst bed. The "regeneration" as used herein refers to the process of coke burning after the completion of cracking and stripping steps of the fluidized bed reactor unit. During the regeneration step, the coke was analyzed using the infrared analyzer.

The desired product (phenolic monomer) yield is calculated with the following equation:

$$\text{product yield, \%} = \frac{\text{desired product(phenolic monomers)weight}}{\text{initial feedstock weight}} \times 100$$

Likewise, the p-cresol dimer conversion may also be calculated with the following equation:

$$p-\text{cresol dimer conversion,} \\ \text{wt \%} = \frac{\text{phenolic monomers} + \text{coke} + \text{gases}}{\text{initial feedstock}} \times 100$$

For this case the p-cresol dimer conversion was about 63.97 wt %, whereas if we include the losses of phenolic monomers also into the conversion equation, then the conversion may reach 68.97%.

Example 2

Fluid catalytic cracking activities of the p-cresol dimer were carried out using a similar procedure as discussed in example 1. The cracking reaction in this case was performed in temperature of 420° C., preferably in 375° C. and the most preferably at 350° C. The phenolic monomers yield data with the variation of cracking temperature is presented in Table 3. The phenolic monomers yield (i.e., 58.97%) is higher at lowest operating temperature of 325° C.

Example 3

Fluid catalytic cracking activities of the p-cresol dimer were carried out using a similar procedure as discussed in example 1. The cracking reaction in this case was performed in temperature of 420° C., preferably in 400° C. and the most preferably at 375° C. The cracking activities at this temperature are presented in Table 3.

Example 4

40 wt % of p-cresol dimer remains unconverted after fluid catalytic cracking. In this embodiment, the unconverted products obtained after first pass in FCC reactor was again used as feed. The products obtained in the first pass reaction were distilled. The fraction above 220° C. is considered as unconverted p-cresol dimers and it is reused as feed for second pass cracking reaction. The fluid catalytic cracking activities of the p-cresol dimer were carried out using a similar procedure as discussed in example 1. The phenolic monomers yield has increased from 58.97% to 77.25% with the recycling of unreacted p-cresol dimer after first pass run. The phenolic monomers yield data with the recycle of unreacted feed in a second pass is presented in Table 4.

The phenolic monomers mainly consist of p-cresol, o-cresol, 2,3-xylenol, and phenol.

The targeted product yield of p-cresol was increased from 29.17% to 38.22% after recycling the unreacted p-cresol dimer in the second pass run, as explained in example 4.

Accordingly, the overall yield of phenolic monomers was increased from 58.97% to 77.25% during the second pass.

While the maximum yield of phenolic monomers from p-cresol dimer was obtained at 325° C. (i.e., ~58.97%) with a single pass run.

E-cat (equilibrium FCC catalyst) has sufficient activity that can be reused for p-cresol dimer cracking activity.

Embodiments of the present disclosure provide numerous benefits. In embodiments, methods of the present disclosure may be suitable to convert undesired products (i.e., p-cresol dimer) of the p-cresol process into phenolic monomers. In embodiments, the equilibrium FCC catalyst, which is the most common catalyst in petroleum refining, may be directly used for catalytic cracking reactions, thus reducing the need for further catalyst development. In embodiments, the present disclosure may help in avoiding the conventional method of p-cresols dimer incineration, thus avoiding environment pollution. In embodiments, the unconverted p-cresol dimer may be recycled to improve conversion.

What is claimed is:

1. A fluid catalytic cracking (FCC) process for producing phenolic monomers from p-cresol dimers, the process comprising:
    (a) charging an equilibrium fluid catalytic cracking catalyst from a hopper of a fluidized bed reactor to a base of the fluidized bed reactor;
    (b) heating the equilibrium fluid catalytic cracking catalyst and the fluidized bed reactor to a predetermined cracking temperature and pressure;
    (c) charging a p-cresol dimer feed to a lower base section of the fluidized bed reactor having an upper outlet section;
    (d) contacting the p-cresol dimer with the equilibrium fluid catalytic cracking catalyst to obtain phenolic monomer vapors;
    (e) condensing the phenolic monomer vapors obtained in (d) to obtain phenolic monomer liquid and fluidization gas;
    (f) separating the phenolic monomer liquid from the fluidization gas to obtain separated phenolic monomer liquid;
    (g) collecting the separated phenolic monomer liquid obtained in (f) to obtain a collected phenolic monomer liquid;
    (h) separating the collected phenolic monomer liquid obtained in (g) into individual phenolic monomers using a distillation apparatus; and
    (i) recycling any unconverted p-cresol dimer obtained (h) into the fluidized bed reactor.

2. The fluid catalytic cracking process of claim 1, wherein the p-cresol dimer comprises, based on the total weight of the p-cresol dimer:

from 40% to 46% by weight 2,2'-methylenebis (4-methylphenol);

from 30% to 36% by weight 1-methyl-2-(4-methylphenoxy)benzene;

from 8% to 12% by weight 2-phenoxybenzoic acid; and from 2% to 4% by weight 4-(phenylmethyl)-phenol.

3. The fluid catalytic cracking process of claim 1, wherein a bottom of the fluidized bed reactor is pre-heated at a temperature from 300° C. to 450° C.

4. The fluid catalytic cracking process of claim 1, wherein the fluid catalytic cracking reaction process is conducted at a reaction pressure from 0.1 atmospheres absolute to 3.0 atmospheres absolute.

5. The fluid catalytic cracking process of claim 1, wherein the equilibrium fluid catalytic cracking catalyst is obtained from a petroleum refinery fluid catalytic cracking process.

6. The fluid catalytic cracking process of claim 1, wherein an amount of equilibrium fluid catalytic cracking catalyst respective to the p-cresol dimer feed is measured as a catalyst-to-oil ratio of 0.1 to 1.0.

7. The fluid catalytic cracking process of claim 1, wherein the p-cresol dimer has a residence time in a bottom of the fluidized bed reactor of from 1.0 seconds to 120.0 seconds.

8. The fluid catalytic cracking process of claim 1, wherein the phenolic monomer liquid is collected in (g) at a temperature from 0° C. to 100° C.

9. The fluid catalytic cracking process of claim 1, wherein separating the collected phenolic monomer liquid into individual phenolic monomers using the distillation apparatus in (h) is conducted at a temperature from 180° C. to 220° C.

* * * * *